United States Patent [19]
Staehle et al.

[11] Patent Number: 6,132,458
[45] Date of Patent: Oct. 17, 2000

[54] METHOD AND DEVICE FOR LOADING A STENT

[75] Inventors: Bradford G. Staehle, Minnetonka; Anthony J. Ferrazzo, New Prague; John H. Burton, Minnetonka, all of Minn.

[73] Assignee: American Medical Systems, Inc., Minnetonka, Minn.

[21] Appl. No.: 09/079,842

[22] Filed: May 15, 1998

[51] Int. Cl.[7] ....................................... A61F 2/06
[52] U.S. Cl. ................... 623/1.11; 623/1.12; 623/1.23
[58] Field of Search ................... 623/1, 12, 1.11, 623/1.12, 1.23; 606/194, 195, 198

[56] References Cited

U.S. PATENT DOCUMENTS

| | | | |
|---|---|---|---|
| 4,655,771 | 4/1987 | Wallsten | 623/1 |
| 5,026,377 | 6/1991 | Burton et al. | 606/108 |
| 5,061,275 | 10/1991 | Wallsten et al. | 623/1 |
| 5,534,007 | 7/1996 | St. Germain et al. | 606/108 |
| 5,630,830 | 5/1997 | Verbeek | 606/198 |
| 5,645,559 | 7/1997 | Hachtman et al. | 606/198 |
| 5,693,089 | 12/1997 | Inoue | 623/1 |
| 5,749,921 | 5/1998 | Lenker et al. | 623/1 |
| B1 4,954,126 | 5/1996 | Wallsten | 600/36 |

*Primary Examiner*—Michael J. Milano
*Assistant Examiner*—Hieu Phan
*Attorney, Agent, or Firm*—Oppenheimer Wolff & Donnelly LLP

[57] ABSTRACT

A device and method for loading a self expanding stent into a deployment tool is disclosed. The device includes an outer tube and a constricting sheath having a stent delivery end and a stent receiving opening opposite thereto. The stent receiving opening is shaped and sized to receive a self expanding stent aligned along the axis and in its expanded state. A funnel, positioned within the constricting sheath, is shaped for collapsing the self expanding stent before loading the stent into the space of the outer tube. An inserter is used to engage and urge the expanded stent into the constricting sheath as the inserter moves towards and into the funnel of the constricting sheath.

6 Claims, 1 Drawing Sheet

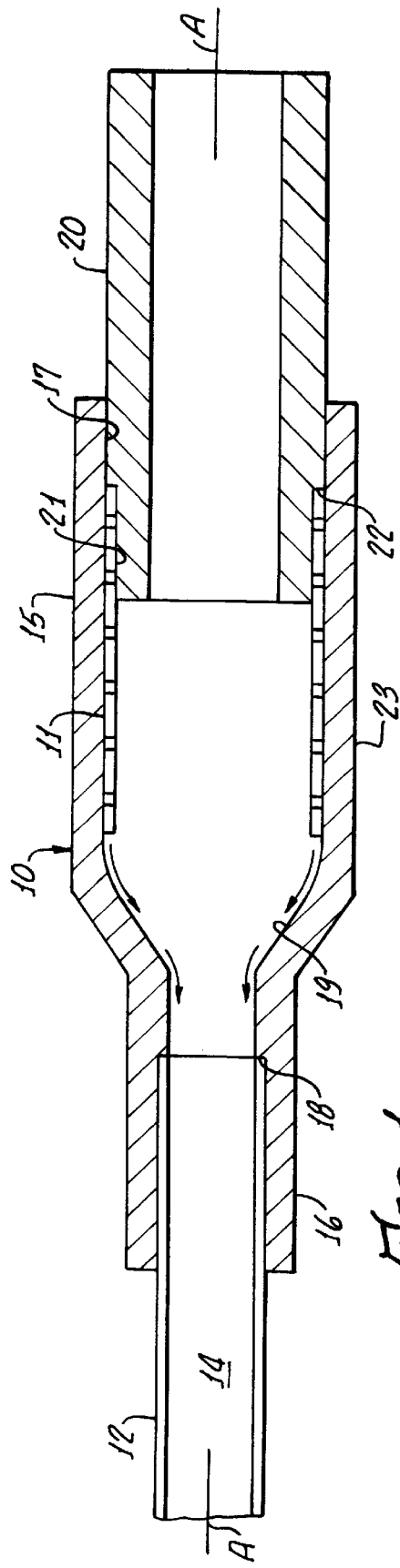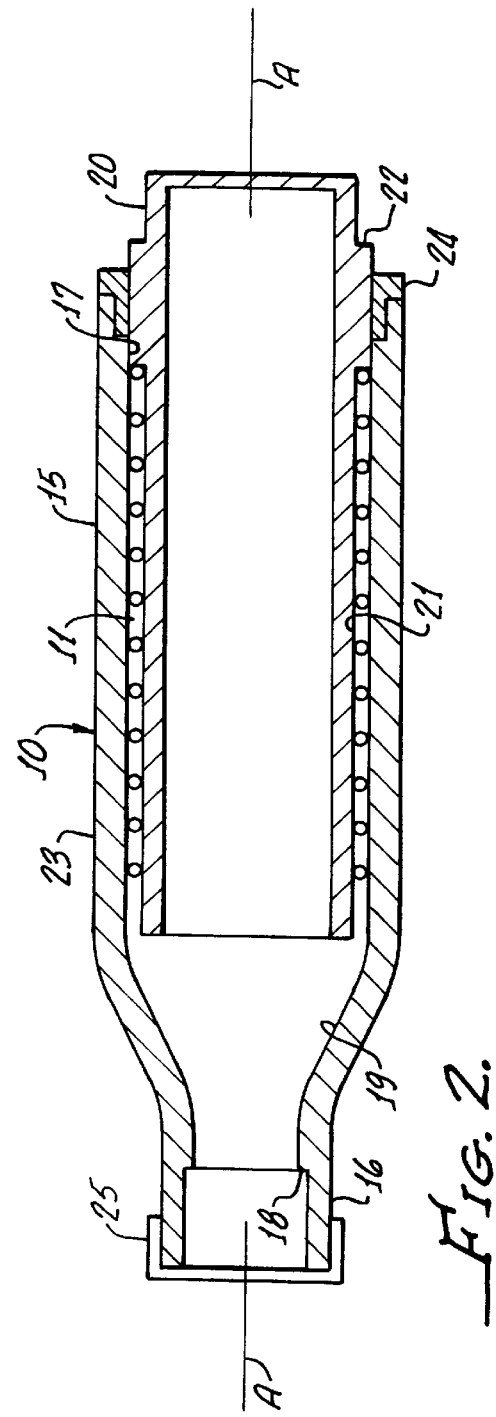

METHOD AND DEVICE FOR LOADING A STENT

This invention relates to a cartridge that stores a self-expanding stent in its expanded state until ready for placement, at which point it is compressed and transferred into a delivery tool.

BACKGROUND OF THE INVENTION

The device may be packaged separately from deployment tool and loaded with a stent in which the stent is then transferred into the deployment tool prior to placement. The deployment tool could be reusable. Also, the stent would not be subjected to compression set due to compression for prolonged period of time.

Self-expanding medical prostheses frequently referred to as stents are well known and commercially available. They are, for example, disclosed generally in the Wallsten U.S. Pat. No. 4,655,771, the Wallsten et al. U.S. Pat. No. 5,061,275 and in Hachtmann et al., U.S. Pat. No. 5,645,559. Stents are used within body vessels of humans for a variety of medical applications. Examples include intravascular stents for treating stenoses, stents for maintaining openings in the urinary, biliary, tracheobronchial, esophageal, and renal tracts, and vena cava filters.

The implantation of an intraluminal stent will preferably cause a generally reduced amount of acute and chronic trauma to the luminal wall while performing its function. A stent that applies a gentle radial force against the wall and that is compliant and flexible with lumen movements is preferred for use in diseased, weakened, or brittle lumens. The stent will preferably be capable of withstanding radially occlusive pressure from tumors, plaque, and luminal recoil and remodeling.

A delivery tool which retains the stent in its radially compressed state is often used to present the stent to a treatment site through tracts, lumens or vessels within the body. The flexible nature and reduced radius of the radially compressed stent enables delivery through relatively small and curved tracts, lumens or vessels. In percutaneous transluminal angioplasty, an implantable endoprosthesis is introduced through a small percutaneous puncture site, airway, or port and is passed through various body vessels to the treatment site. After the stent is positioned at the treatment site, the delivery tool is actuated to release the positioned stent. The stent is allowed to self-expand within the body vessel. The delivery tool is then removed from the patient. The stent remains in the vessel at the treatment site as an implant. Typically the delivery tool is designed for single use and so it is thrown away.

Stents must exhibit a relatively high degree of biocompatibility since they are implanted in the body. An endoprosthesis may be delivered into a body tract, vessel or lumen on or within a surgical delivery tool as shown in U.S. Pat. Nos. 4,954,126 and 5,026,377. Preferred delivery tools for the present invention may include modifications of those delivery tools so that there cooperate and interact with the present invention.

Commonly used materials for known stent filaments include Elgiloy and Phynox metal spring alloys. Other metallic materials than can be used for self-expanding stent filaments are 316 stainless steel, MP35N alloy, and superelastic Nitinol nickel—titanium. Another self expanding stent, available from Schneider (USA) Inc. of Minneapolis, Minn., has a radiopaque clad composite structure such as shown in U.S. Pat. No. 5,630,830 to Mayer. Self-expanding stents can be made of a Titanium Alloy. The strength and modulus of elasticity of the filaments forming the stents are also important characteristics. Elgiloy, Phynox, MP35N and stainless steel are all high strength and high modulus metals. Nitinol has relatively low strength and modulus but includes temperature dependent self expanding or superelastic properties that have benefits.

There is continued growth in procedures and applications of self-expanding stents with particular characteristics for use in various medical indications. Stents are needed for implantation in an ever increasing list of lumens and vessels throughout the patient's body. Different physiological environments are encountered and it is recognized that there is no universally acceptable set of stent characteristics.

High health care costs demand medical devices that can be sterilized and reused but heretofore stent delivery instruments were supplied by their manufacturers loaded with a stent and thus prepared for a single use and then disposal. That approach was acceptable for the introduction of stent vascular and lumenal surgery but was not cost effective. The need for equipment and techniques for loading stents into a delivery tool has not been addressed so that medical practitioners can do so in the preoperating room environment. Moreover the use of a sterilizable reusable delivery tool depends on an easy and effective loading device and fool proof method of use.

SUMMARY OF THE INVENTION

A device for loading a self expanding stent into a deployment tool may have an outer tube defining a space. The device might include a constricting sheath with a stent delivery end and a stent receiving opening opposite thereto. The constricting sheath is preferably open therethrough with the stent delivery end and the stent receiving opening aligned along an axis thereof. There is an outer tube on the deployment tool. The stent delivery end is most preferably shaped and sized for slipping over the outer tube. The stent receiving opening might be shaped and sized to receive a self expanding stent aligned along the axis and in its expanded state. A rest within the delivery end can possibly be located for seating the constricting sheath along the axis and in position over the outer tube. A funnel is preferably positioned within the constricting sheath located between the stent delivery end and the stent receiving opening. The funnel is most preferably shaped for collapsing the self expanding stent before loading into the space of the outer tube. An inserter may be depressed for movement along the axis and within the constricting sheath towards the space. The inserter could have a stent carrying shaft to support the expanded stent thereabout and cantilever therefrom. A shoulder on the stent carrying shaft engages the expanded stent for most preferably urging the expanded stent into the constricting sheath as the inserter moves towards and into the funnel of the constricting sheath. A method for using the device includes the steps of slipping over the outer tube, seating the constricting sheath along the axis and in position over the outer tube and against the rest, collapsing the self expanding stent before loading into the space of the outer tube in the funnel, carrying the stent on the stent carrying shaft cantilever therefrom, depressing the inserter for movement along the axis and within the constricting sheath towards the space of the outer tube, and engaging the stent with the shoulder for urging the expanded stent into the constricting sheath as the inserter moves towards and into the funnel.

Using a deployment tool with the handle in the deployed position, the constricting sheath is slipped over the deployment tool outer tubing until tubing rests against sheath. By depressing device inserter towards deployment tool, the device moves towards and into a necked down funnel section of the constricting sheath and comes in contact with an inserter stop. The device pushes the inserter back into the outer tubing and device is gripped between outer tube and inserter tube is retracted drawing device into outer tubing. When collapsible device is completely inside outer tube, the constructing sheath may be removed and the device is ready for deploying.

BRIEF DESCRIPTION OF THE DRAWINGS

FIG. 1 shows in cross section a device for loading a self expanding stent into a deployment tool having an outer tube defining a space.

FIG. 2 shows in cross section a cartridge for the device for loading a self expanding stent into a deployment tool having an outer tube defining a space but it is shown in its shipping position and not its loading position.

DETAILED DESCRIPTION OF THE DRAWINGS

In FIG. 1 a device 10 for loading a self expanding stent 11 into a deployment tool 12 is shown. The deployment tool 12 has an outer tube 13 defining a space 14. The device 10 has a constricting sheath 15 with a stent delivery end 16 and a stent receiving opening 17 opposite thereto. The constricting sheath 15 is open therethrough with the stent delivery end 16 and the stent receiving opening 17 aligned along an axis "A" thereof. The stent delivery end 16 is shaped and sized for slipping over the outer tube 13. The stent receiving opening 17 is shaped and sized to receive the self expanding stent 11 aligned along the axis "A" and in its expanded state, see FIGS. 1 and 2. A rest 18 within the stent delivery end 16 is located for seating the constricting sheath 15 along the axis "k" and in position over the outer tube 13. A funnel 19 is positioned within the constricting sheath 15 located between the stent delivery end 16 and the stent receiving opening 17. The funnel 19 is shaped for collapsing the self expanding stent 11 before loading into the space 14 of the outer tube 13. An inserter 20 is depressed for movement along the axis "A" and within the constricting sheath 15 towards the space 14. The inserter 20 has a stent carrying shaft 21 to support the expanded stent 11 thereabout and cantilever therefrom. A shoulder 22 on the stent carrying shaft 21 engages the expanded stent 11 for urging the expanded stent 11 into the constricting sheath 15 as the inserter 20 moves towards and into the funnel 19 of the constricting sheath 15. The rest 18 is sized to constrain the stent 11 slightly more than the space 14 of the outer tube 13. The constricting sheath 15 can be a cartridge 23 for the delivery of the stent 11 into the space 14 of a deployment tool 12. A pilot bushing 24 is positioned in the stent recieving opening 17 to support and guide the inserter 20 along the axis "A" as best seen in FIG. 2. A cover 25 fits over the stent delivery end 16 so the cover 25, the inserter 20, the pilot bushing 24 and the constricting sheath 15 form the sealed cartridge 23. In FIG. 2 the inserter 20 is shown in its shipping position. To use this configuration to deliver the expandable stent 11 into the funnel 19, the inserter 20 is pulled out along axis "A", reversed and inserted into the expandable stent 11. Thus, shoulder 22 in FIG. 2 is shown outside the cartridge 23. This approach may be necessary for a polymeric or bioresorbable stent that cannot be stored for any length of time in its collapsed state.

A method for using the device 10 includes slipping over the outer tube 13 the constricting sheath 15, seating the constricting sheath 15 along the axis "A" and in position over the outer tube 11 and against the rest 18, collapsing the self expanding stent 11 before loading into the space 14 of the outer tube 13 in the funnel 19, carrying the expandable stent 11 on the stent carrying shaft 21 cantilever therefrom, depressing the inserter 20 for movement along the axis "A" and within the constricting sheath 15 towards the space 14 of the outer tube 13, and engaging the stent 11 with the shoulder 22 for urging the expanded stent 11 into the constricting sheath 15 as the inserter 20 moves towards and into the funnel 19.

What is claimed is:

1. A device for loading a self expanding stent into a deployment tool having an outer tube defining a space, the device comprising:

a constricting sheath with a stent delivery end and a stent receiving opening opposite thereto, the constricting sheath open therethrough with the stent delivery end and the stent receiving opening aligned along an axis thereof, the stent delivery end shaped and sized for slipping over the outer tube, the stent receiving opening shaped and sized to receive a self expanding stent aligned along the axis and in its expanded state;

a rest within the delivery end located for seating the constricting sheath along the axis and in position over the outer tube;

a funnel positioned within the constricting sheath located between the stent delivery end and the stent receiving opening, the funnel shaped for collapsing the self expanding stent before loading into the space of the outer tube;

an inserter depressed for movement along the axis and within the constricting sheath towards the space of the outer tube, the inserter having a stent carrying shaft (21) to support the expanded stent thereabout and cantilever therefrom, and a shoulder on the stent carrying shaft to engage the expanded stent for urging the expanded stent into the constricting sheath as the inserter moves towards and into the funnel of the constricting sheath.

2. The device of claim 1 wherein the rest is sized to constrain the stent slightly more than the space of the outer tube.

3. The device of claim 1 wherein the constricting sheath is a cartridge for the delivery of the stent into the space of a deployment tool.

4. The device of claim 3 wherein a pilot bushing is positioned in the stent recieving opening to support and guide the inserter along the axis.

5. The device of claim 4 wherein a cover fits over the stent delivery end so the cover, the inserter, the pilot bushing and the constricting sheath form a sealed cartridge.

6. A method for using a device for loading a self expanding stent into a deployment tool having an outer tube defining a space, the method have the steps of:

slipping over the outer tube a constricting sheath with a stent delivery end and a stent receiving opening opposite thereto, the constricting sheath open therethrough with the stent delivery end and the stent receiving opening aligned along an axis, the stent receiving opening shaped and sized to receive a self expanding stent aligned along the axis and the stent in its expanded state;

seating the constricting sheath along the axis and in position over the outer tube and against a rest located within the delivery end;

collapsing the self expanding stent before loading into the space of the outer tube in a funnel positioned within the constricting sheath between the stent delivery end and the stent receiving opening;

carrying the stent on a stent carrying shaft to support the expanded stent thereabout and cantilever therefrom;

depressing an inserter for movement along the axis and within the constricting sheath towards the space of the outer tube, and engaging the stent with a shoulder on the stent carrying shaft for urging the expanded stent into the constricting sheath as the inserter moves towards and into the funnel of the constricting sheath.

* * * * *